United States Patent [19]

English

[11] Patent Number: 5,259,236
[45] Date of Patent: Nov. 9, 1993

[54] TRIBOMETER

[76] Inventor: William English, 1050 Lovely La., Ft. Meyers, Fla. 33903

[21] Appl. No.: 888,842

[22] Filed: May 27, 1992

[51] Int. Cl.⁵ .............................................. G01N 19/02
[52] U.S. Cl. ......................................................... 73/9
[58] Field of Search ......................................... 73/7-10

[56] References Cited

U.S. PATENT DOCUMENTS

| | | |
|---|---|---|
| 2,299,895 | 10/1942 | Harrall et al. |
| 2,955,455 | 10/1960 | Frederik |
| 3,020,744 | 2/1962 | Long |
| 3,098,377 | 7/1963 | Beauchamp |
| 3,427,859 | 2/1969 | Taub ........................................ 73/7 |
| 3,721,115 | 3/1973 | Kearns |
| 4,081,989 | 4/1978 | Majcherczyk |
| 4,130,007 | 12/1978 | Hayashi .................................... 73/7 |
| 4,173,885 | 11/1979 | Matlock |
| 4,798,080 | 1/1989 | Brungraber |
| 4,895,015 | 1/1990 | English |

OTHER PUBLICATIONS

Murphy, "Crutch or Cane Tip Slippage on Wet Tile vs. Velocity at Contact" Draft Revision—Not Dated.
Slipping Cane and Crutch Tips—Part I—Static Performance of Current Devices; Leon Bennett, M. A. E. and Eugene F. Murphy, Ph.D., Bulletin of Prosthetics Research for 1977, pp. 71-90.

Primary Examiner—Robert Raevis
Attorney, Agent, or Firm—Dickstein, Shapiro & Morin

[57] ABSTRACT

A tribometer which approximately duplicates the forces exerted on a test surface by a human foot or cane tip during the walking process. The force exerted on the test surface by a test specimen is provided by a fluid actuated cylinder supplied with a compressed fluid. This force is applied during a sufficiently short period of time so as to avoid the absorbtion and squeegee effects normally encountered when testing wet surfaces. The coefficient of friction for the test surface is then determined by measuring the angle of incidence at which the test specimen will slip when brought into contact with the test surface.

17 Claims, 8 Drawing Sheets

TRIBOMETER

BACKGROUND OF THE INVENTION

The present invention relates to a tribometer for testing the slip resistance of various surfaces. More particularly, the present invention relates to a portable variable incidence tribometer, for measuring the slip resistance of wet or oily surfaces as well as dry, which approximates the forces present during the walking process.

A tribometer is a device used for measuring surface friction. Tribometric devices utilize various methods for determining the frictional force present when one surface is pulled or pushed across another under a certain predetermined pressure. These devices fall within three generally recognized categories; (1) dragsled, (2) articulated strut and (3) pendulum type testers. Numerous tribometric devices in each category exist, which are disclosed in a number of United States Patents, which test the frictional forces between different dry surfaces.

One problem which exists and which is not overcome by these devices is obtaining consistent surface friction results on surfaces which are wet or have lubricating contaminants thereon. Because of the increased risk of slippage which exists when a surface is wet a reliable method of testing these surfaces is needed.

In situations where it is desired to determine the slip resistance of a wet surface unreliable results can occur due to the effects of absorbtion and squeegeeing. These effects result in devices where the test specimen is allowed to rest on the test surface prior to motion testing so that the contaminants are either absorbed by the test specimen or squeezed out from beneath it.

Attempts have been made to provide devices which can reliably test the slip resistance on different surfaces including wet surfaces. These attempts are described as follows.

U.S. Pat. No. 4,798,080 discloses a portable apparatus which tests the slip resistance of surfaces by substantially instantaneously applying a load to a frictional pad. The load in this device is applied using a gravity dropped weight or a spring.

U.S. Pat. No. 4,895,015 discloses a portable horizontal slipmeter in which a stationary pull mechanism applies a force to a drag sled. The drag sled with the test specimen attached is held away from the test surface until the device is actuated.

Leon Bennett, M.A.E. and Eugene F. Murphy, Ph.D., *Slipping Cane and Crutch Tips*, bulletin of prosthetics research for 1977, page 71, discloses an instrumented walking cane used for testing the slip resistance of cane tips on various walking surfaces. Instrumentation is provided on this device to show the angle of incidence and magnitude of the force vector at the point where the cane tip slips.

It has also been suggested to provide a variable incidence mast fitted with an articulated cane that is thrust downward at a predetermined angle in order to test the slip resistance of a cane tip. This device utilizes an electric solenoid to provide the downward thrust.

The prior art devices have many limitations. In particular, the devices which employ weights, springs or solenoids for the thrust force are not representative of the forces which are present during the walking process.

Additionally, the devices which require the application of thrust force by the operator are subject to operator dependent variables. These operator dependent variables tend to bias the results of the slip tests so that consistent results are difficult to achieve.

A further limitation exists in devices which utilize gravitational force. This limitation results in the inability to obtain valid results on inclined surfaces without recalibration. Since it is often necessary to determine the coefficient of friction of an inclined surface, this inability substantially limits the application of these devices.

SUMMARY OF THE INVENTION

The disadvantages of the prior art are alleviated to a great extent by the present invention which provides a tribometer, which approximates the forces present during walking, having a compressed fluid supply means, a cylinder means for converting the fluid pressure into a linear force, a means for attaching a test specimen to the cylinder means, a means for actuating the cylinder means, a means for adjusting the angle of incidence of the test specimen with the test surface and a means for determining the angle of incidence where the test specimen slips.

In one aspect of the invention, a tribometer is provided which utilizes a compressor to create a fluid pressure which can then be stored. When the device is properly actuated, the stored fluid pressure is supplied to a cylinder which converts this pressure into a linear force. A test specimen (which can be a cane tip) is attached to the cylinder by a plug and is thereby brought into contact with the test surface at varying angles of incidence to determine at what angle the test specimen slips.

In other aspects of the invention the compressor may be replaced by a compressed gas cartridge. Further, the test specimen may be attached to the cylinder by a ball and socket arrangement or swivel joint.

In utilizing fluid pressure in accordance with the tribometer of the present invention a method of determining slip resistance on lubricated or dry surfaces is achieved which more closely approximates the forces present during walking. Since the present invention operates using fluid pressure in a self contained system, rather than gravity, it can achieve consistent results on both level and inclined surfaces and is not subject to operator independent variables.

It is an object of the present invention to provide a consistent and reliable method of testing the coefficient of friction of different surfaces including wet surfaces.

It is a further object of the present invention to provide a device which measures the slip resistance of surfaces under conditions which more closely approximate the forces present in a human foot or cane tip during the walking process.

It is a further object of the present invention to provide a device which can accurately test the slip resistance on inclined surfaces.

Additional objects and advantages of the invention will be set forth in part in the description which follows, and in part will be obvious from the description, or may be learned by practice of the invention. The objects and advantages of the invention will be obtained by means of instrumentalities and combinations particularly pointed out in the appended claims.

DETAILED DESCRIPTION OF PREFERRED EMBODIMENTS

Figure 1:
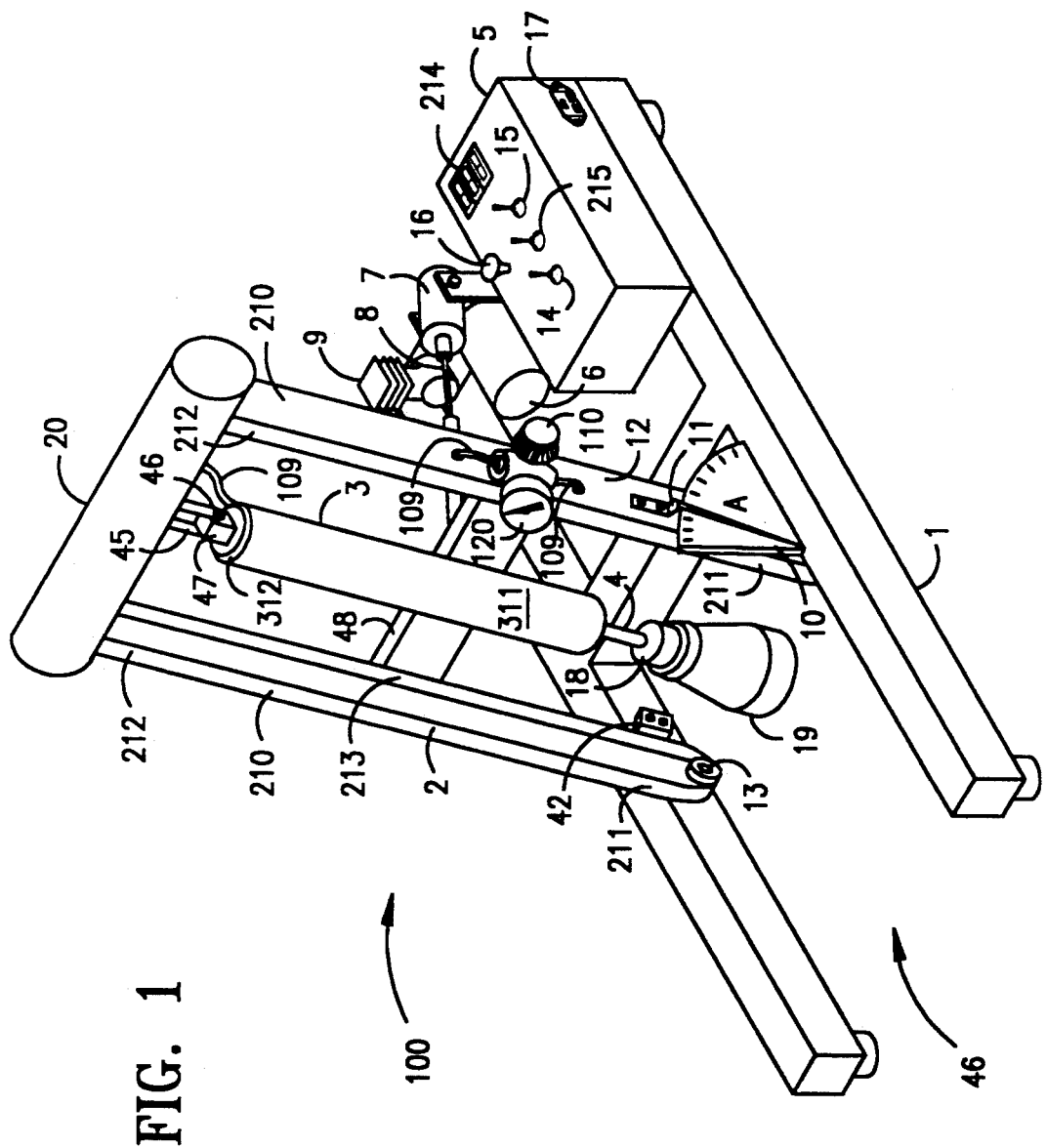
FIG. 1 is an isometric view of a tribometer according to a preferred embodiment of the present invention.

Refer now to FIG. 1, there being shown a tribometer, generally designated by reference number 100, in accordance with a preferred embodiment of the present invention. The tribometer 100 is constructed of a frame 1 onto which the remaining elements of the tribometer are mounted. Those elements include a compressed fluid supply means for creating a fluid pressure, a cylinder means for converting the fluid pressure into a linear force, an attachment means for attaching a specimen 19 to the cylinder means, an actuating means for actuating the cylinder means to move the test specimen in contact with a test surface, an adjustment means for adjusting the angle of incidence at which the test specimen is brought into contact with the test surface, and a means for determining the angle of incidence.

The compressed fluid supply means includes an air compressor 9 which is driven by a compressor driver motor 6. Ambient air is drawn into the compressor 9 and the discharged compressed air is delivered through conduits 109 to an air pressure receiver 20. Conduits 109 are partially hidden from view in FIG. 1 but the paths of the conduits of the pneumatic circuit are described in detail below with reference to FIG. 4. Receiver 20 holds a volume of compressed air, which volume is sufficient to drive cylinder 3 for one operating cycle during operation of the tribometer 100. An adjustable pressure regulator 12 and gauge 120 is positioned in the conduits 109 between a gas cylinder 3 and the air pressure receiver 20. The regulator 12 monitors the pressure in the cylinder 3 and indicates the pressure through a gauge 120 to the user. The user may adjust the regulator using knob 110.

A fluid valve 33 is positioned in the pneumatic circuit of conduits 109 between the receiver 20 and the gas cylinder 3. When the valve 33 is opened by depressing button 16 the compressed air stored in receiver 20 expands and then a portion of the compressed air is delivered through conduits 109 and regulator 12 and, at a regulated pressure, to cylinder 3.

Figure 3:
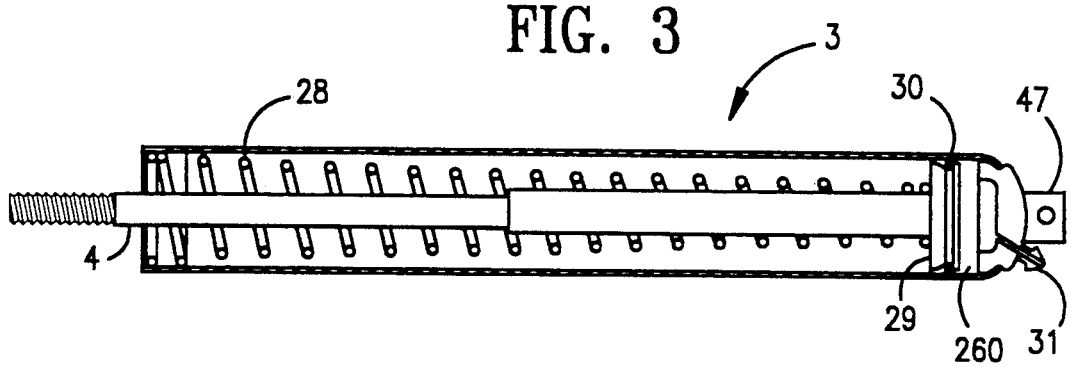
FIG. 3 is a cross sectional view of a gas actuated cylinder used in the tribometer of FIG. 1.

The cylinder means for converting the fluid pressure to a linear force is depicted in FIG. 3 and includes a gas actuated cylinder 3, a piston 29 and a piston rod 4 connected to the piston 29. The operation of the cylinder means is explained in more detail below with respect to FIG. 3.

The specimen 19 is attached to the cylinder means by an attachment means which includes, in the embodiment of FIG. 1, a crutch end plug 18. Plug 18 approximates the size and shape of the end of a crutch shaft used to aid a person in walking. The specimen 19 will be driven in contact with the test surface 46 on which the tribometer 100 is placed. The dynamic friction between a variety of test specimens 19 and test surfaces can be measured by varying the combination of the specimens 19 and the test surfaces.

The adjusting means includes a mast assembly 2 which has two arms 210, each of which are connected at their respective frame ends 211 to the frame 1 such that they are pivotable on mast assembly hinge pins 13. Each of the two arms 210 of the mast assembly 2 is connected at its respective distal end 212 to an air pressure receiver 20. A support bracket 48 extends between and is connected to each of the two arms 210 of the mast assembly 2 at positions 213 on the arms 210 located about midway between the respective ends 211 and 212. The support bracket 48 provides rigidity to the mast assembly 2 and provides a mounting point for the mast angle adjustment means, as described in detail below.

Two connecting tabs 45 are mounted to the air pressure receiver 20 at a location between the two ends 212 of the arms 210. A cylinder mounting lug 47 is attached at a pivot end 312 of a gas actuated cylinder 3 and is mounted between the connecting tabs 45 on a hinge pin 46 such that lug 47 and cylinder 3 can pivot with respect to tabs 45 and receiver 20. Extending downward from a piston end of the gas actuated cylinder 3 is a piston rod 4 onto which a crutch end plug 18 is connected. A test specimen 19 is then mounted onto the crutch end plug 18.

A protractor 10 is mounted to the frame 1 in the proximity of the frame end 211 of one arm 210 of the mast assembly 2. The angle A which the mast assembly forms with the frame 10, and thus with the test walking surface with which the frame is generally parallel, can be thus determined by means of an inclination angle pointer 11 mounted to the arm 210 of the mast assembly 2.

Figure 2:
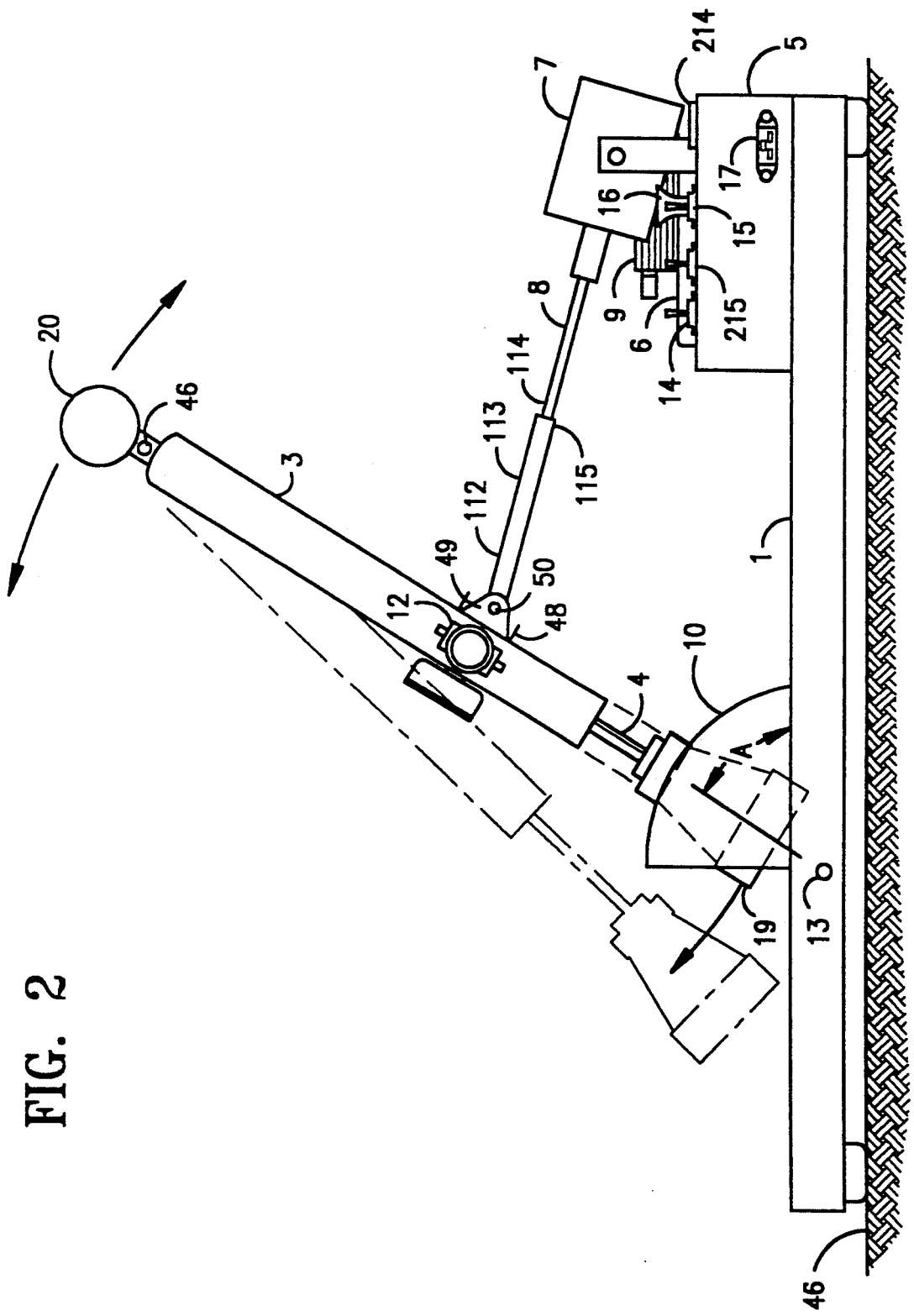
FIG. 2 is a side view of portions of the tribometer of FIG. 1.

Referring to FIG. 2, a mounting bracket 49 is connected to the support bracket 48. A hinge pin 50 extends through the bracket 48 and the mast end 112 of an axis adjustment jack screw assembly 8 to pivotably connect the mast end 112 to the bracket 49 and thereby to the mast 2 (FIG. 1). The assembly 8 includes a threaded rod 114 which threads into a threaded socket in the threaded end 115 of rod 113. The rod 114 is driven either clockwise or counter-clockwise by the adjustment motor 7, thereby lengthening the effective length of rods 113 and 114 to pivot the mast 2 on hinge pins 13 to adjust the inclination angle A of the mast 2.

Figure 5:
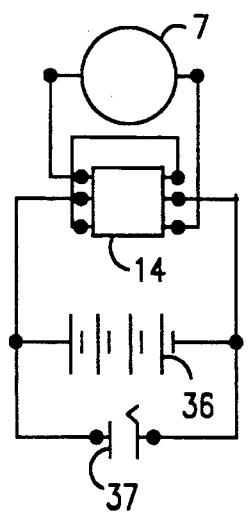
FIG. 5 is a schematic illustration of the electrical circuit employed in the axis angle regulation mechanism of the tribometer of FIG. 1.

The circuit for driving the adjustment motor 7 is illustrated in FIG. 5. The circuit includes a double pole double throw axis angle regulator switch 14 which is connected to the mast access adjustment motor 7. A battery 36 which can be recharged using the battery charger jack 37 provides the energy for driving the mast axis adjustment motor 7.

The construction of the gas actuated cylinder 3 is illustrated in FIG. 3. The cylinder 3 has a piston 29 which is normally urged in the direction of the cylinder mounting lug 47 by a spring 28. The gas actuated cylinder 3 is connected to the air pressure receiver 20 (FIG. 1) through a compressed gas line fitting 31 (FIG. 3) and a connecting hose 109 (FIG. 1). As compressed air is released from the air pressure receiver 20 (FIG. 1) the compressed air fills chamber 260 and begins pressing against the piston 29 and piston seal 30 driving the piston 29 in a direction away from the cylinder mounting lug 47.

When the piston 29 is driven away from the cylinder mounting lug 47, the test specimen 19 and crutch end plug 18 which are connected to the piston rod 4 are thereby driven downward so that the test specimen 19 will come in contact with the floor or surface to be tested.

The air pressure which is maintained in the air pressure receiver 20 is generated by the air compressor 9 (FIG. 1). The air pressure supply (FIG. 4) has a compressor driver motor 6 which drives the air compressor 9. The air compressor 9 will supply air pressure to the air pressure receiver 20 with excess pressure being exhausted through the pressure relief valve 32. When the cycle start button is pressed, air pressure contained in the air pressure receiver 20 will be released through the conduits 109 and the pressure regulator 12, which controls the pressure, into the gas actuated cylinder 3.

Figure 4:
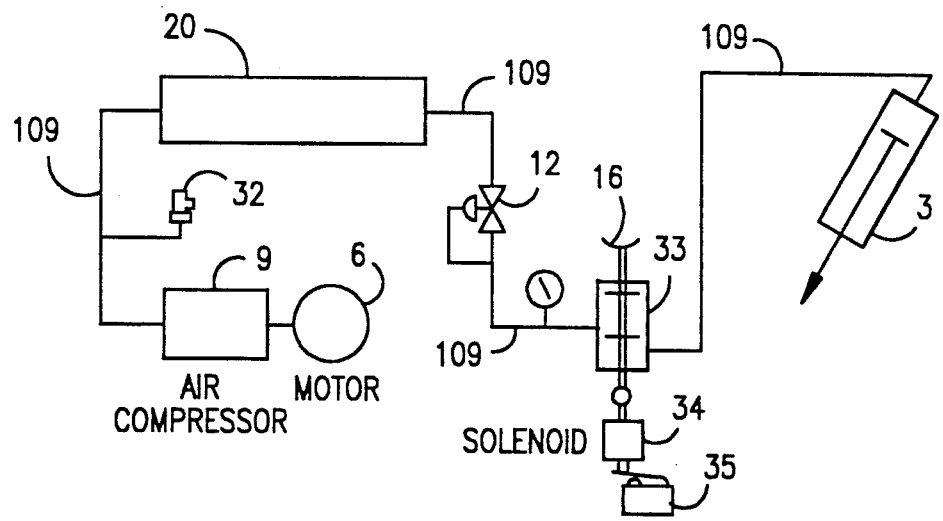
FIG. 4 is a schematic illustration of the pneumatic system of the tribometer of FIG. 1.

The electronic timer start switch 35 which actuates the solid state delay electronic timer 38 (FIG. 6) will also be actuated when the cycle start button 16 is pressed. The timer 38 allows sufficient time for piston rod 4 (FIG. 1) to travel downward so that the slip test may be performed before the valve return solenoid 34 (FIG. 6) is actuated. When the valve return solenoid 34 is actuated, it closes the operating selector valve 33 removing the air pressure from the gas actuated cylinder 3 and vents the cylinder chamber (FIG. 4). Upon venting the cylinder chamber, the force of the spring 28 returns the piston to its original position.

Figure 6:
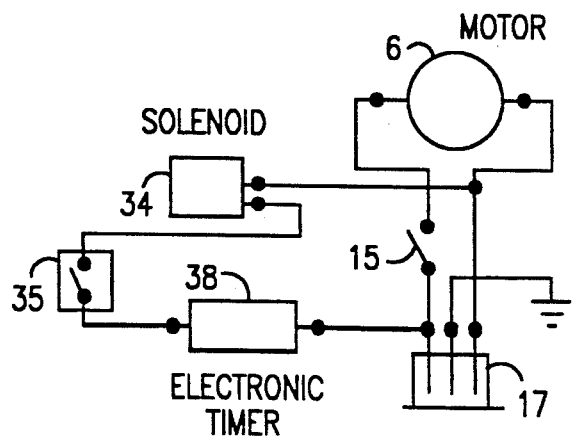
FIG. 6 is a schematic illustration of the electrical circuit for the tribometer of FIG. 1.

The compressor drive motor 6 is driven by current supplied to the power cord receptacle 17 (FIG. 6). The compressor drive motor 6 is turned on and off by means of a compressor start switch 15 installed on one leg of the compressor drive motor supply.

The operation of the tribometer of FIG. 1 to determine the coefficient of friction between a test specimen and a test surface can be understood by referring to FIG. 4. When the button 16 is pressed opening the fluid valve 33 fluid will begin to flow through conduits 109 and regulator 12 into the chamber 260 (FIG. 3) of the fluid actuated cylinder 3.

Referring now to FIG. 3, when the fluid pressure in the chamber 260 exceeds the force of the spring 28, the piston 29 will move away from the cylinder mounting lug 47. As the pressure in the chamber 260 continues to increase, the piston 29 will continue to move in this direction until the test specimen 19 (FIG. 2) comes into contact with the test surface 46 (FIG. 2).

After the test specimen has contacted the test surface the fluid pressure in the cylinder 3 will continue to build to a maximum pressure determined by the regulator 12. In this way the present invention approximates the dynamics of the forces present during the walking process wherein a foot or cane tip is first placed on the ground with a nominal pressure and thereafter the pressure is increased as weight is shifted onto the foot or cane.

In the embodiment of FIG. 1 the pressure build time between when the test specimen 19 first comes into contact with the test surface 46 and when full pressure has built up in the chamber 260 and the test specimen, if it is going to slip, has begun to slip, is less than or equal to approximately one tenth of a second. The duration of this pressure build time is important for approximating the human walk. The pressure build time should be short enough to substantially alleviate the problems of absorbtion of moisture and squeegeeing of moisture out from between the test surface and test specimen on wet surfaces. The gravity drop and solenoid driven systems for measuring slip resistance cannot duplicate this action since all of the force between the test specimen and test surface is applied substantially instantaneously in those systems. In contrast, in the present invention, the specimen contacts the test surface more gently than gravity or solenoid activation permits. After initial contact of the test foot with the test surface, the vector force builds up rapidly but smoothly in a manner similar to the human walking gait, whereas the gravity and solenoid actuated devices initial contact is a rather spiked impact, and the vector force drops off sharply, rather than rising after contact, as it does in human ambulation. Because the force vector is applied by gas pressure, rather than gravity, the present invention can be used on ramps and sloped surfaces without recalibration, whereas gravity devices must be used only on level surfaces or they must be recalibrated for the particular slope under test. Unlike gravity operated articulated strut devices, the vector force is constant at any angle. In the gravity devices, the force declines progressively as the angle decreases. Further, the rate of decline is not linear, rising sharply at relatively acute angles with the horizontal.

Moreover, the use of the pneumatic system provides flexibility in adjusting the pressure build time. The pressure in the receiver 20, the flow diameter of the conduits 109, and other flow resistance passageways, the tension and spring rate of the spring 28 can all be adjusted to vary the maximum force and the pressure build time.

Figure 9:
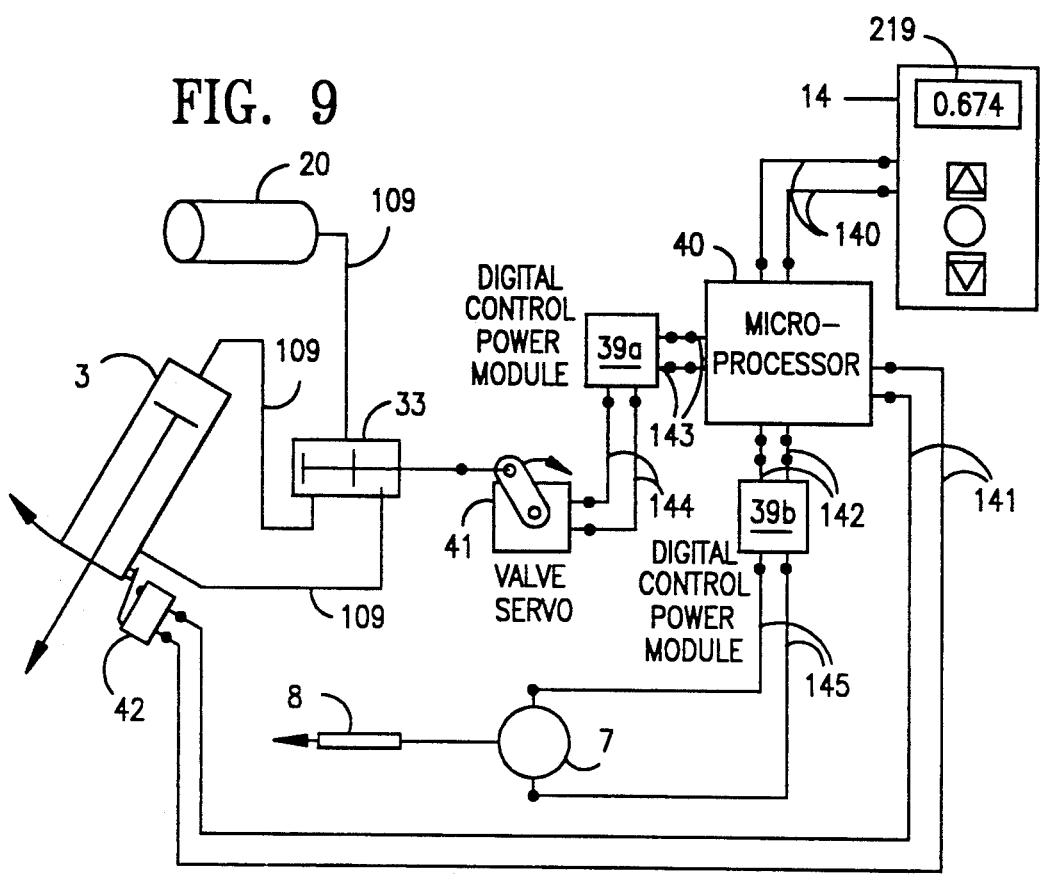
FIG. 9 is a schematic illustration of a circuit for calculating and displaying the coefficient of friction for the tribometer of FIG. 1.

Alternatively the steps of actuating the gas actuated cylinder 3, resetting the inclination angle of the mast for each progressive testing of a specific test surface 26 and test specimen 19, determining the angle at which the test specimen 19 will slip and calculating the coefficient of friction of the test specimen 19 can all be performed by a microprocessor 40 (FIG. 9). By providing power to the microprocessor 40 via operation select switch 215, the manual operation steps described previously will be performed automatically.

With the gas actuated cylinder 3 starting at a specific inclination angle the operating selector valve 33 will be depressed by valve servo 41. This valve servo 41, is actuated by signals sent by the digital control power module 39a through data lines 144. The digital control module 40 is in turn controlled by the microprocessor through signals sent through data lines 143.

The test specimen 19 will now be forced towards the test surface 26 at which time the test specimen 19 will either slip or will not slip. If the test specimen 19 does not slip, the proximity switch 42 will remain closed and operation of the microprocessor will not be interrupted.

The microprocessor will then adjust the inclination angle of the mast assembly 2 by a predetermined amount, such as one degree. The microprocessor adjusts this angle through signals sent to the digital control power module 39b across data lines 142. The digital control power module then drives the mast axis adjustment motor 7, through signals sent across data lines 145, which in turn drives the axis adjustment jack screw assembly 8.

The microprocessor actuates the valve servo 41 again to actuate the gas actuated cylinder 3. Again the test specimen 19 is forced towards the test surface 46 and the switch 42 determines whether the test specimen 19 slips at the new inclination angle. This process will be repeated until the test specimen slips, whereupon the proximity switch 42 is opened and the operation of the microprocessor 40 is interrupted. The microprocessor then determines, from the angle which the test specimen 19 slipped, the coefficient of friction of the test specimen 19 and will generate an appropriate signal to output. This result is then sent to the digital display 214 across data lines 140 and indication of the angle and/or coefficient of friction is displayed to the user.

Refer now to FIG. 2. After the test specimen has come in contact with the floor or test surface 26 onto which the tribometer is placed, if the force exerted by the cylinder is sufficient to overcome the frictional force between the test specimen 19 and the test surface 26, the specimen 19 will slip and the cylinder 3 will pivot at the cylinder hinge pin 46. The angle at which the test specimen 19 is brought in contact with the test surface 26 can then be varied by the access adjustment jack screw assembly 8 until a point is reached where the test specimen 19 no longer slips when the gas actuated cylinder 3 is actuated. The angle A at which the test specimen 19 no longer slips can then be determined by use of the inclination angle pointer 11 and protractor 10 and the coefficient of friction ($C_f$) thereby determined. One formula for determining the coefficient of friction is $C_f = \tan A$.

Figure 7:
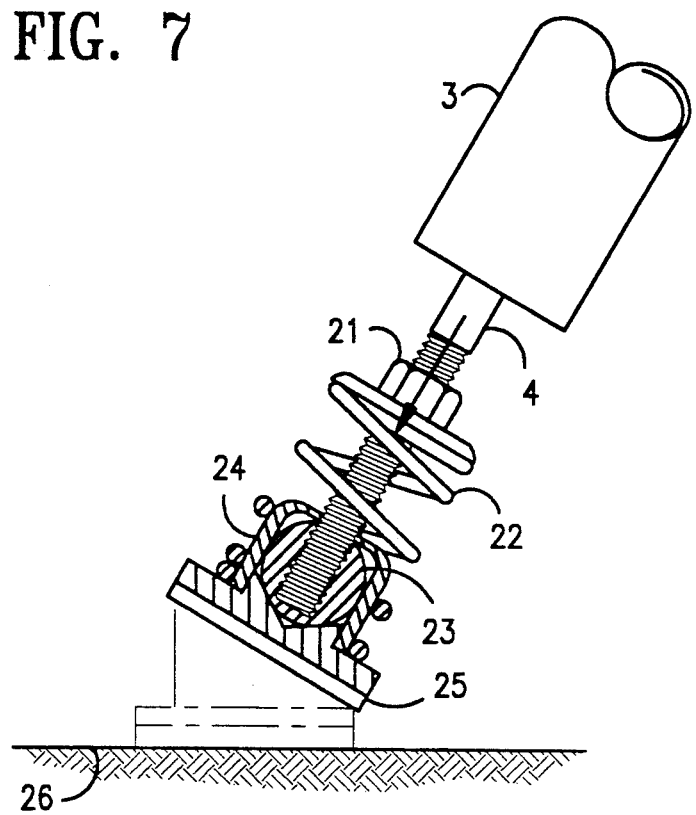
FIG. 7 is a partial cut-away side view showing an alternate preferred embodiment of a tester used in the tribometer of FIG. 1.

Refer now to FIG. 7 which illustrates an alternate embodiment of the attachment means for attaching the test specimen to the cylinder means. In the embodiment of FIG. 3, a ball joint arrangement is substituted for the crutch end plug 18 of the embodiment of FIG. 1. The universal ball joint of this embodiment includes a ball 23 which is affixed to the threaded end of the piston rod 4. The universal ball joint socket 24 rotates about this ball and a spring 22 is placed between the universal ball joint socket 24 and a spring stiffness adjusting nut 21. The spring 22 maintains the cylinder pad 25 which is attached to the base of the universal ball joint socket 24, perpendicular to the piston rod 4. The tension of the spring 22 can be adjusted by rotating the spring stiffness adjusting nut 21. The slider pad 25 is held at an angle to the test floor surface 26 until the slider pad 25 comes in contact with the test floor surface 26. Once the slider pad 25 comes in contact with the test floor surface 26 the universal ball joint socket 24 will rotate around the universal ball joint 23 bringing the slider pad 25 down flat onto the test floor surface.

Figure 8:
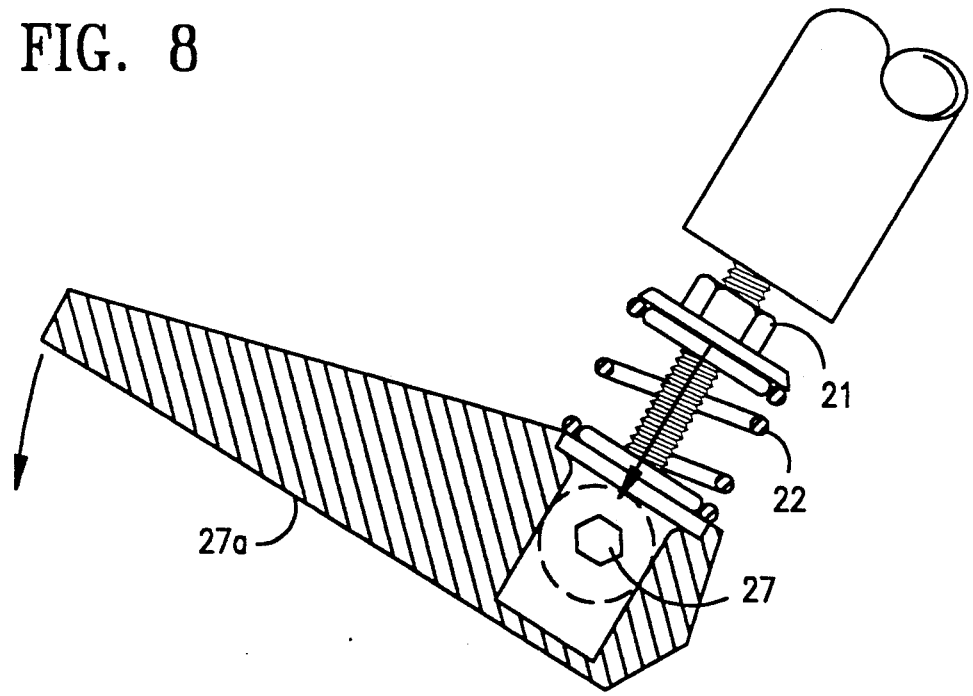
FIG. 8 is a view like FIG. 7 showing another alternate preferred embodiment of a tester.

In another embodiment of the invention, the universal ball joint depicted in FIG. 7 is replaced by a foot mold 27a and swivel joint 27 (FIG. 8). The foot mold 27a is chosen to approximate the action of a shoe being placed on the test surface during walking. In this embodiment the foot mold 27a is connected to the piston rod 4 through the swivel joint 27. The spring 22 and spring stiffness adjustment nut 21 are again used to maintain the foot mold 27a at an angle to the test floor surface 26 until such time as the foot mold 27a comes in contact with the test floor surface 26. Upon coming into contact with the test floor surface 26, the foot mold 27a will rotate so that it will become flush with the test floor surface 26. This embodiment of the invention can be used for slip testing of shoes mounted on the mold or shoe sole materials mounted directly on the mold.

Figure 10:
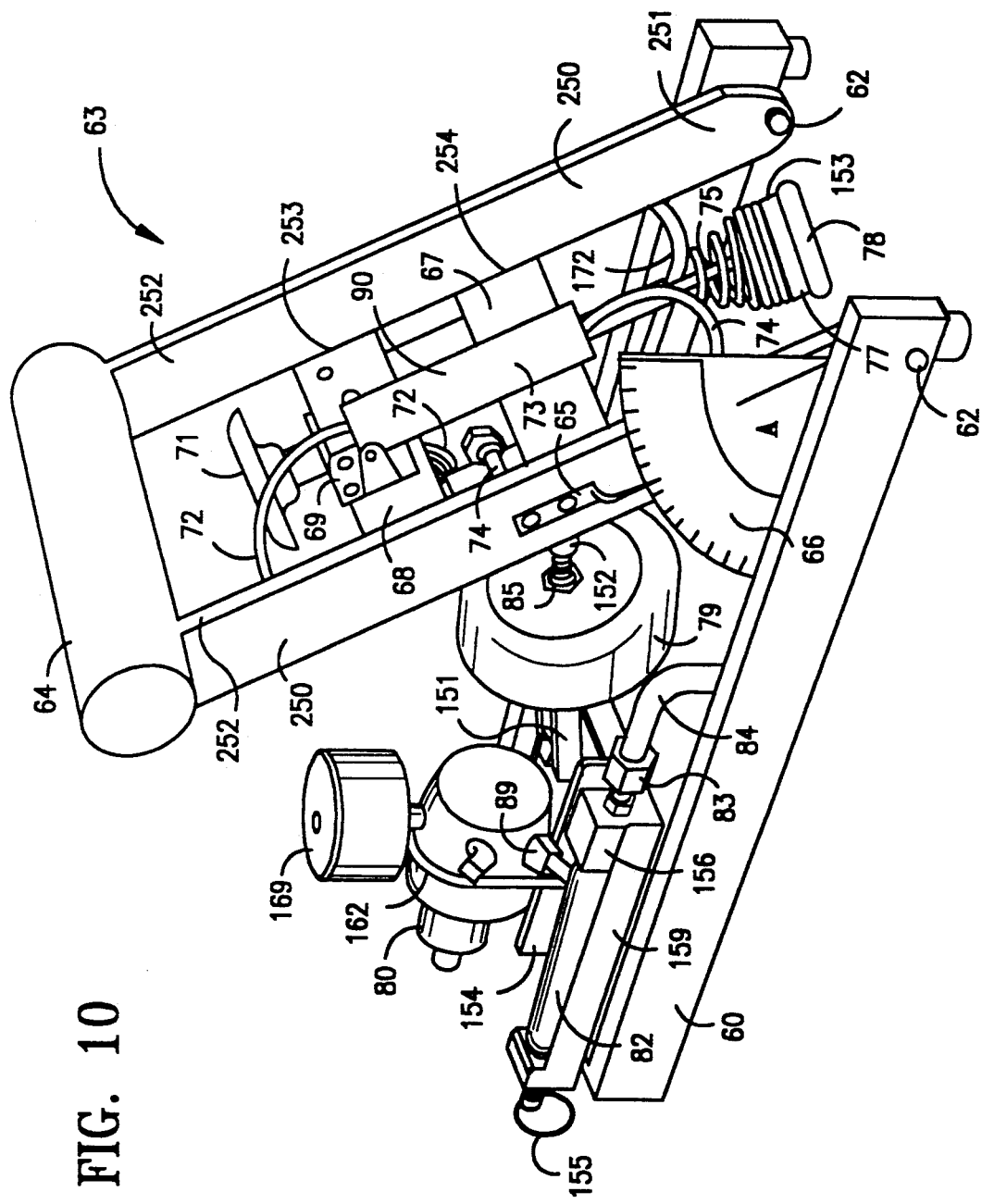
FIG. 10 is an isometric view of a tribometer according to a second preferred embodiment of the present invention.

In yet another embodiment of this invention depicted in FIG. 10 the use of electrical devices is eliminated. In this embodiment, the two support arms 250 of the mast 63 are pivotably connected to the frame 60 by mast assembly hinge pins 62. The ends of the support arms 252 of the mast 63 are connected to a handle 64.

An inclination angle pointer 65 is attached to one arm of the mast assembly 63 to indicate the angle of inclination and coefficient of friction on a protractor segment 66 having a compound scale. A support member 68 is mounted between the support arms 253 below the handle and onto which a mounting bracket 69 is attached. The gas actuated cylinder 73 is further pivotably attached to the mounting bracket 69 at its distal end 90 and rests against a second support bracket 67 which is mounted between the support arms 254 below the first support member 68.

The piston rod 75 of the gas actuated cylinder 73 has a universal ball joint 76 (FIG. 14) attached at the operational end. As depicted in FIG. 14 a universal ball joint socket bottom section 77 having an outer threaded surface 168 is screwed into the threaded inner surface of the universal ball joint socket upper section 157 to form a universal ball joint socket around the universal ball joint 76. The material to be tested 78 (FIG. 13) is mounted to the bottom surface of the universal ball joint socket bottom section 77. By providing a two part universal ball joint socket the material to be tested 78 can easily be changed by unscrewing the universal ball joint socket bottom section and replacing it with a another one having a different testing material mounted to it.

Figure 13:
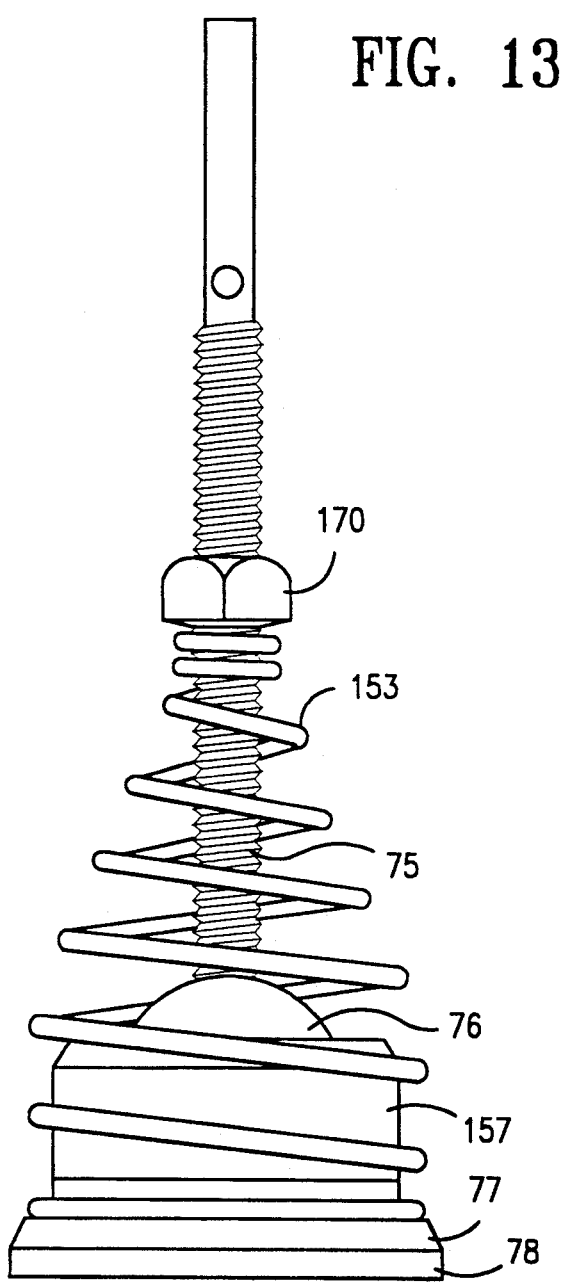
FIG. 13 is a view of a changeable tester for the tribometer of FIG. 10.
Figure 14:
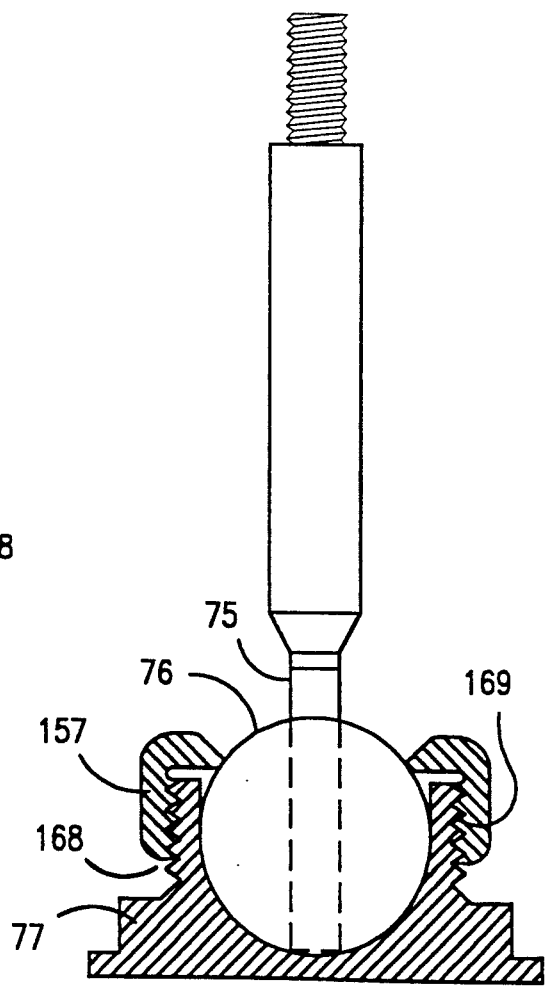
FIG. 14 is a partial cut-away view of the changeable tester of FIG. 13.

As depicted in FIG. 13 a compression spring 153 having a general conical shape can be fitted to the tester between the universal ball joint socket bottom section 77 and an spring stiffness adjusting nut 170. This compression spring 153 provides resistance to the flexion of the ball joint and returns the test shoe to zero incidence from the force vector for each test.

Figure 12:
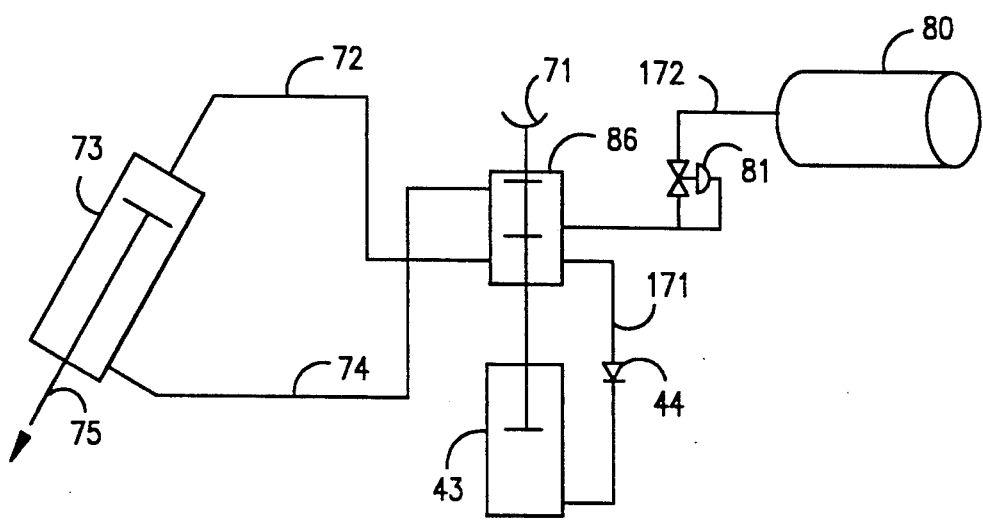
FIG. 12 is a schematic illustration of the pneumatic circuit for driving the gas actuated cylinder in the tribometer of FIG. 10.

Turning now to FIG. 12 when the cycle start button 71 is depressed, the double action operation selector valve 86 which is maintained within housing 158 (FIG. 11) is opened allowing gas pressure from the gas pressure receiver 80 to flow through feed hose 172, as regulated by the pressure regulator 81, through the selector valve 86 and into the gas actuated cylinder 73 through the feed hose 72. At the same time, gas will also flow through selector valve 86 into the secondary actuating cylinder 43 through the pneumatic logic control cycle timer 44. When sufficient pressure has built up in the secondary actuating cylinder 43, the operating selector valve 86 will be forced closed and the gas actuated cylinder will be vented through feed hose 74, causing the piston rod 75 to retract.

Figure 11:
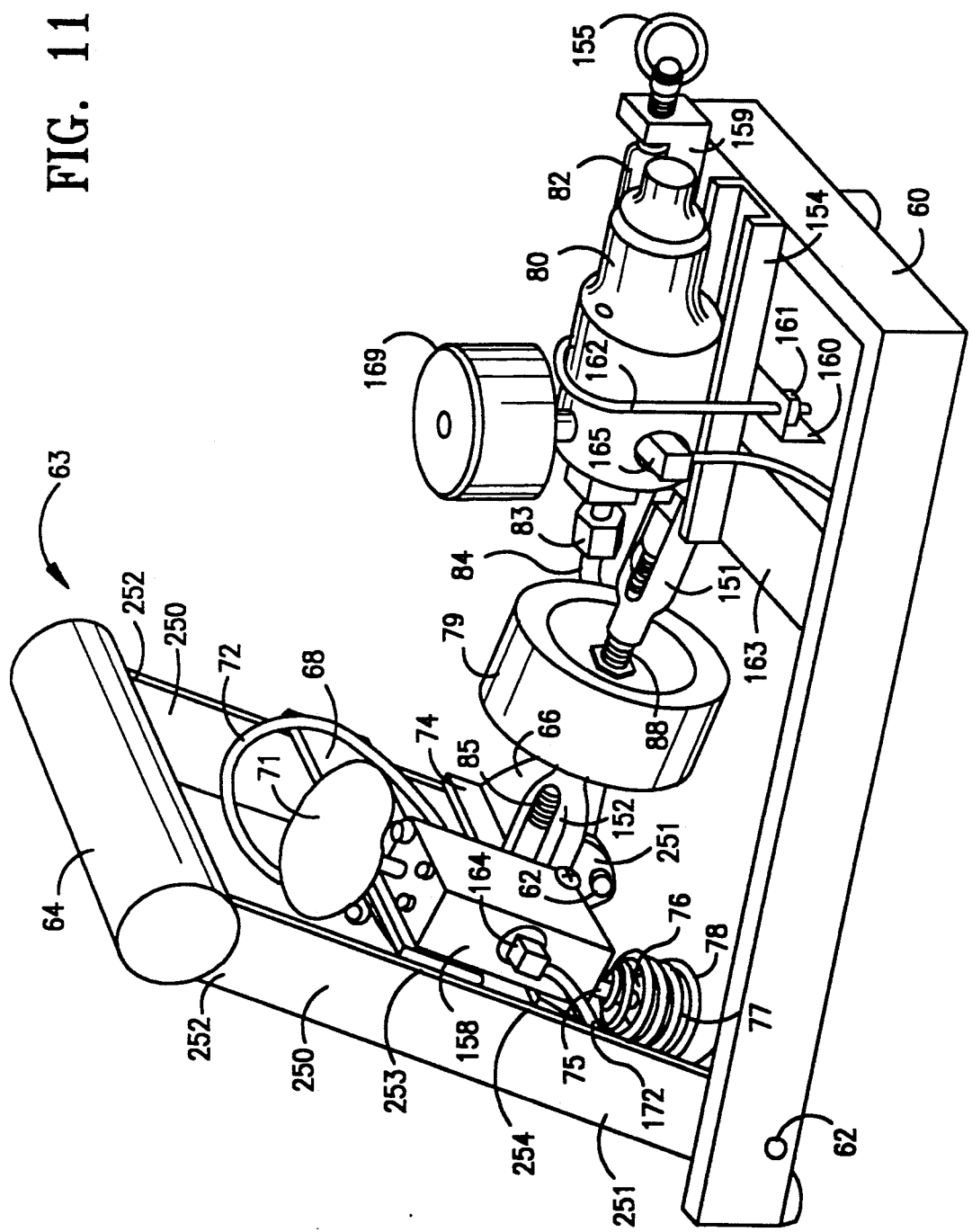
FIG. 11 is an isometric view of the tribometer of FIG. 10 as viewed from a different angle.

The inclination angle of the mast assembly 63 in this embodiment can be adjusted by turning the mast axis adjustment knob 79 depicted in FIG. 11. The rod which is attached to the adjustment knob 79 has right handed threading on one end 85 and is screwed into a turnbuckle 152 which is pivotally attached to the support bracket 67. The other end of the rod 88 has left handed threading and is screwed into a turnbuckle 151 which is pivotally attached to mounting bracket 154. By manually turning the mast axis adjustment knob 79, either clockwise or counterclockwise, the effective lengths of rod ends 85 and 88 will change causing the mast 63 to pivot on hinge pins 62 adjusting the inclination angle A of the mast 63.

Gas pressure is supplied to the air pressure receiver 80 by a compressed gas vessel 82 such as a currently available $CO_2$ cartridge used for $CO_2$ rifles and other devices. When the compressed gas cartridge 82 is inserted into the cartridge holder 159 and the cartridge lock 155 is tightened gas will be supplied through the block 156. The compressed gas will then flow into the gas pressure receiver 80 through the feed pipe 84 which is connected to the block by fitting 83 and to the gas pressure receiver 80 by a fitting 89. The pressure in the gas pressure receiver is indicated by a pressure gauge 169.

Because its principle of operation is ergonomically analogous to the human walking stride, the coefficient of friction indications of the present invention are more valid than those of other articulated strut testers, especially on wet or lubricated surfaces. The present invention is the only one that can test the slip-resistance of footwear products on in situ walking surfaces under real world environmental conditions. Because of its compact size and absence of the gravity weights characteristic of other static coefficient of traction testers, the present invention is lighter and more easily portable than any of the recognized slipmeters now in use. Because the present tester does not have to be leveled, calibrated or adjusted to the test surface before use, it is easier and faster to use than other testers requiring such preliminary operations.

The above descriptions and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed as new and desired to be protected by Letters Patent of the United State is:

1. A tribometer which approximates the forces exerted on a test surface by a human foot or cane tip during the walking process, comprising:
   compressed fluid supply means for creating a fluid pressure;
   cylinder means for converting the fluid pressure into a linear force;
   attachment means for attaching a test specimen to the cylinder means;
   actuating means for actuating the cylinder means so as to bring the test specimen in contact with the test surface;
   adjustment means for adjusting an angle of incidence in which the test specimen is brought into contact with the test surface; and
   measuring means for determining the angle of incidence at which said test specimen slips.

2. A tribometer as in claim 1, wherein said compressed fluid supply means and said cylinder means are constructed such that there is a pressure build time after the test specimen has contacted the test surface during which the fluid pressure in the cylinder means will continue to build to a maximum pressure.

3. A tribometer as in claim 2, wherein the pressure build time is more than substantially instantaneous and less than or equal to approximately one-tenth of a second.

4. A tribometer as in claim 1, wherein the attaching means includes a universal ball joint and socket.

5. A tribometer as in claim 4, wherein said universal ball socket, to which said test specimen is attached, is readily exchangeable.

6. A tribometer as in claim 1, wherein the attaching means includes a swivel joint.

7. A tribometer as in claim 6, wherein said attaching means includes a foot mold so that slip testing of shoes can be performed.

8. A tribometer as in claim 1, wherein the adjusting means includes a jack screw assembly.

9. A tribometer as in claim 1, wherein said compressed fluid supply means includes regulating means for regulating the pressure applied by compressed fluid supply means.

10. A tribometer as in claim 9, wherein the regulating means is adjustable such that the magnitude of the pressure applied by the compressed fluid supply means can be varied.

11. A tribometer as in claim 10, wherein the compressed fluid supply means includes a compressed gas cylinder.

12. A tribometer as in claim 10, wherein the compressed fluid supply means includes an air compressor.

13. A tribometer as in claim 1, wherein said fluid is a gas.

14. A tribometer as in claim 1, wherein the actuating means includes a fluid valve.

15. A tribometer as in claim 14, wherein said actuating means includes a valve servo for actuating the fluid valve.

16. A tribometer as in claim 1, wherein said measuring means includes a protractor mounted in a position to measure the angel of incidence.

17. A tribometer as in claim 1, further comprising a calculating means and display means for calculating and displaying the coefficient of friction for the tested surface.

* * * * *